| United States Patent [19] | [11] | 4,447,649 |
|---|---|---|
| Breuninger | [45] | May 8, 1984 |

[54] PROCESS FOR THE MANUFACTURE OF CITRAL

[75] Inventor: Manfred W. Breuninger, Freiburg, Fed. Rep. of Germany

[73] Assignee: Hoffmann-La Roche Inc., Nutley, N.J.

[21] Appl. No.: 423,761

[22] Filed: Sep. 27, 1982

Related U.S. Application Data

[63] Continuation of Ser. No. 304,723, Sep. 23, 1981.

[30] Foreign Application Priority Data

Oct. 31, 1980 [CH] Switzerland .......................... 8124/80

[51] Int. Cl.$^3$ ....................... C07C 45/00; C07C 47/21
[52] U.S. Cl. ..................................... 568/484; 568/460
[58] Field of Search ......................... 568/484, 460, 485

[56] References Cited

U.S. PATENT DOCUMENTS 3,631,188  12/1971  Wakamatus et al. ............... 568/484

FOREIGN PATENT DOCUMENTS 51229  5/1982  European Pat. Off. ............ 568/484

OTHER PUBLICATIONS

Craig et al., "J. Amer. Chem. Society", vol. 83, p. 1871+ (1961).
Smith, "The Chemistry of Open-Chain Organic Nitrogen Compounds", vol. II, pp. 26-27 (1966).
Lecher et al., "J. Amer. Chem. Society", vol. 70, (1948) p. 3789+.
Sweeley et al., "J. Amer. Chem. Society", vol. 79 (1957) p. 2620+.
Michelot, Bull. Soc. Chim. France 12, pp. 4377-4385 (1969).
Renaud and Leitch, Can. J. Chem. 46, 385-390 (1968).
Ferles, Coll. Czech. Chem. Comm. 36 (12) 4103 (1971).
Janot C. R., Acad.Sc. Paris t. 265, p. 669 (1967).

*Primary Examiner*—Werren B. Lone
*Attorney, Agent, or Firm*—Jon S. Saxe; George M. Gould; William H. Epstein

[57] ABSTRACT

The invention is concerned with a novel process for the manufacture of citral from an N-oxide.

4 Claims, No Drawings

PROCESS FOR THE MANUFACTURE OF CITRAL

This is a continuation of application Ser. No. 304,723 filed Sept. 23, 1981.

SUMMARY OF INVENTION

In accordance with this invention, it has been discovered that a citral compound of the formula

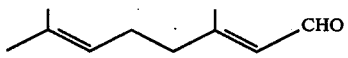

can be obtained by reacting a compound of the formula

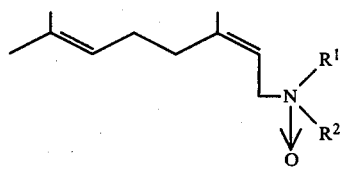

wherein $R^1$ and $R^2$ are the same or different $C_{2-6}$-alkyl substituents, or $R^1$ and $R^2$ taken together with the N-atom is a $C_{4-6}$-cyclic group, with an anhydride of a $C_{2-6}$-alkanecarboxylic acid.

BACKGROUND OF INVENTION

The citral compound of formula I designates citral as all of its isomers, i.e. neral and geranial as well as mixtures of these compounds. The Z-form or the E-form of the compound of formula II may be used as starting materials.

Also, mixtures of these E and Z forms can be used as the starting materials of formula II. The ratio of E/Z has little influence on the course of the reaction or on the yield. These starting materials of formula II are known or can be prepared according to methods known per se.

Suitably, $R^1$ and $R^2$ are ethyl or propyl or $R^1$ and $R^2$ together with the N-atom represent piperidino, pyrrolidino or perhydroazepin.

$R^1$ and $R^2$ preferably represent ethyl.

The preferred $C_{2-6}$-alkanecarboxylic acid is acetic acid. Anhydrides are formed also with $C_{2-6}$ alkane carboxylic acids.

The reaction in accordance with the invention can be carried out under acidic or basic conditions, namely either with the aid of, for example, one of the aforementioned acids as the solvent or, for example, with the addition of a liquid tertiary amine (e.g. triethylamine, diethylmethylamine, pyridine, etc.).

Conveniently, the compound of formula I is placed in one of the aforementioned acids or one of the foregoing amines and the acylating agent is slowly added thereto at a temperature of −20° to 20° C., especially 0° to 20° C. However, temperature is not critical, and any suitable temperature can be used to carry out the reaction of this invention. Furthermore, the mole ratio of the compound of formula II to the acylating agent is also not critical and any convenient mole ratio can be used in carrying out this reaction. However, the molar ratio of the compound of formula II to acylating agent that is preferred is 1:1–5, with the ratio 1:3–5 being especially preferred.

The reaction in accordance with the invention is thereupon carried out, conveniently at a temperature between 0° and 100° C., preferably between 20° and 60°. The course of the reaction can be followed, for example, by gas chromatography.

For the working-up, an extraction agent (e.g. an ether) and water are added to the reaction mixture. Furthermore, the presence of a buffer substance such as a bicarbonate and an alcohol (e.g. i-propanol) has been found to be advantageous.

The following Example illustrates the present invention:

EXAMPLE

| Educt | Reaction Procedure | Working-Up | Yield % |
|---|---|---|---|
| (1) | a | A | 51.4–53.7* |
| (1) | b | A | 44.9 |
| (1) | e | D | 40 |
| (2) | c | B | 42.5 |

(1) 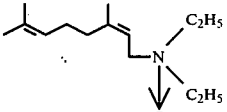 1 g (4.44 millimol)

(2) 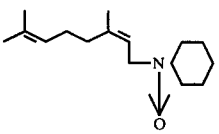 1.g (4.21 millimol)

*4 reactions (a) Dissolution of the educt in 2.0–3.5 g (20–35 mmol) of triethylamine; cautious addition of 1.5–2.5 g (15–25 mmol) of acetic anhydride or propionic acid anhydride at 0° to room temperature while stirring; further stirring at 40°–50° C. for 60 to 240 minutes. Yields using the geranyl derivative or a 1:3 mixture of neryl/geranyl derivative analogue.

(b) Dissolution of the educt in 1 g (16.7 mmol) of glacial acetic acid; cautious addition of 1.5 g (15 mmol) of acetic anhydride at 0° while stirring; further stirring at 50° for 240 minutes.

(c) As under (b), but with addition of the anhydride and further stirring at room temperature.

(e) Addition of 0.13 g (1.5 mmol) of anhydrous sodium acetate as a buffer; rapid addition of 2.5 g (25 mmol) of acetic anhydride without cooling, a strong exothermic reaction occurring; further stirring for 5 minutes.

(A) Addition of 0–10 ml of diethyl ether to the reaction mixture, followed by 10 ml of water, 5–20 of i-propanol and 5–10 g of sodium bicarbonate; stirring at 40°–50° for 60 minutes; extraction 3–5 times with diethyl ether, gas-chromatographic analysis with the addition of beta-cyclocitral as the standard.

(B) As (A), but without the addition of i-propanol.

(D) As (A), product isolation by chromatography of the concentrated extract on silica gel using a mixture of hexane/ether (1:1) as the elution agent.

I claim:

1. A process for the manufacture of a citral compound of the formula which process comprises reacting at a temperature of from 0° C. to 100° C. a compound of the formula

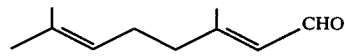

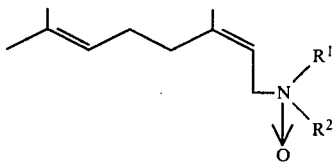

wherein $R^1$ and $R^2$ are the same or different $C_{2-6}$-alkyl substituent or $R^1$ and $R^2$ together with the N-atom is a $C_{4-6}$-cyclic group, with an anhydride of a $C_{2-6}$-alkanecarboxylic acid.

2. A process according to claim 1, wherein $R^1$ and $R^2$ represent ethyl.

3. A process of claim 1 wherein the anhydride is acetic anhydride.

4. The process of claim 1 where the citral compound is neral and said compound is in its Z-form.

* * * * *